United States Patent
Brand et al.

(10) Patent No.: US 10,952,599 B2
(45) Date of Patent: Mar. 23, 2021

(54) ACTIVE LENS DEFOGGING FOR DIGITAL IMAGING SYSTEMS

(71) Applicant: Ricoh Company, Ltd., Tokyo (JP)

(72) Inventors: Jonathan Frieman Brand, San Jose, CA (US); Noah Denis Bedard, Pacifica, CA (US); Manuel Martinello, Mountain View, CA (US)

(73) Assignee: Ricoh Company, LTD., Tokyo (JP)

( * ) Notice: Subject to any disclaimer, the term of this patent is extended or adjusted under 35 U.S.C. 154(b) by 310 days.

(21) Appl. No.: 15/703,670

(22) Filed: Sep. 13, 2017

(65) Prior Publication Data

US 2019/0076010 A1 Mar. 14, 2019

(51) Int. Cl.

| A61B 1/227 | (2006.01) |
| A61B 1/12 | (2006.01) |
| A61B 1/00 | (2006.01) |
| H04N 5/225 | (2006.01) |
| G02B 23/24 | (2006.01) |

(52) U.S. Cl.
CPC .......... *A61B 1/127* (2013.01); *A61B 1/00096* (2013.01); *A61B 1/227* (2013.01); *G02B 23/2446* (2013.01); *H04N 5/22541* (2018.08); *A61B 1/00064* (2013.01); *H04N 2005/2255* (2013.01)

(58) Field of Classification Search
CPC ...................................................... A61B 1/227
USPC ................................ 600/199, 200, 245–249
See application file for complete search history.

(56) References Cited

U.S. PATENT DOCUMENTS

| 4,942,629 | A | 7/1990 | Stadlmann |
| 7,311,660 | B2 | 12/2007 | Gomez |
| 7,648,234 | B2 | 1/2010 | Welchel et al. |
| 8,939,967 | B2 | 1/2015 | Raksi |
| 9,392,933 | B2 | 7/2016 | Bedard et al. |
| 9,565,996 | B2 | 2/2017 | Berkner et al. |
| 2009/0185191 | A1* | 7/2009 | Boppart ............... A61B 5/0066 356/479 |
| 2013/0128223 | A1* | 5/2013 | Wood ................. A61B 1/00186 351/206 |
| 2014/0088366 | A1* | 3/2014 | Solingen ............ A61B 1/00135 600/169 |
| 2014/0200406 | A1* | 7/2014 | Bennett ................ A61B 1/0646 600/109 |
| 2014/0316238 | A1 | 10/2014 | Berkner et al. |
| 2017/0119237 | A1 | 5/2017 | Bedard et al. |

* cited by examiner

*Primary Examiner* — Amy R Sipp
(74) *Attorney, Agent, or Firm* — Fenwick & West LLP (57) ABSTRACT

A lightfield otoscope includes a housing with a tip configured to receive a disposable speculum. The otoscope also includes a microlens array, a sensor array and an optical train contained within the housing. The optical train includes an objective lens and a relay lens. The objective lens is positioned at least partially within the tip. The relay lens is used to relay an image plane of the objective lens to the microlens array and to relay a pupil plane of the objective lens to the sensor array. An active heating element is also contained within the housing and positioned to heat the front surface, thereby reducing fogging and/or condensation on the front surface.

16 Claims, 8 Drawing Sheets
(2 of 8 Drawing Sheet(s) Filed in Color)

ACTIVE LENS DEFOGGING FOR DIGITAL IMAGING SYSTEMS

BACKGROUND

1. Technical Field

This disclosure relates generally to lens defogging of digital imaging systems, including lightfield otoscopes.

2. Description of Related Art

Digital camera systems are sometimes required to work in extreme environmental conditions. These environmental conditions include high temperatures and relative humidity, such as in a body cavity, where temperatures can reach 45° C. (113° F.). The relative humidity is a function of environment, and in vivo the relative humidity can reach 100%.

A lightfield otoscope is a clinical imaging system that collects 3D information about the patient's ear canal. The lightfield otoscope's primary imaging target is the tympanic membrane. The otoscope is required to work in a high-temperature and high-humidity environment. If a patient has a high fever in a wet season, common environmental factors associated with disease states, fog and condensation may form on the front surface of the lightfield otoscope during the exam. The fog will prevent capture of good quality images of the ear drum.

SUMMARY

In one aspect, a lightfield otoscope includes a housing with a tip configured to receive a disposable speculum. The otoscope also includes a microlens array, a sensor array and an optical train contained within the housing. The optical train includes an objective lens and a relay lens. The objective lens is positioned at least partially within the tip. The relay lens is used to relay an image plane of the objective lens to the microlens array and to relay a pupil plane of the objective lens to the sensor array. An active heating element is also contained within the housing and positioned to heat the front surface, thereby reducing fogging and/or condensation on the front surface.

Other aspects include components, devices, systems, improvements, methods, processes, applications, computer readable mediums, and other technologies related to any of the above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure have other advantages and features which will be more readily apparent from the following detailed description and the appended claims, when taken in conjunction with the accompanying drawings, in which:

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1A:
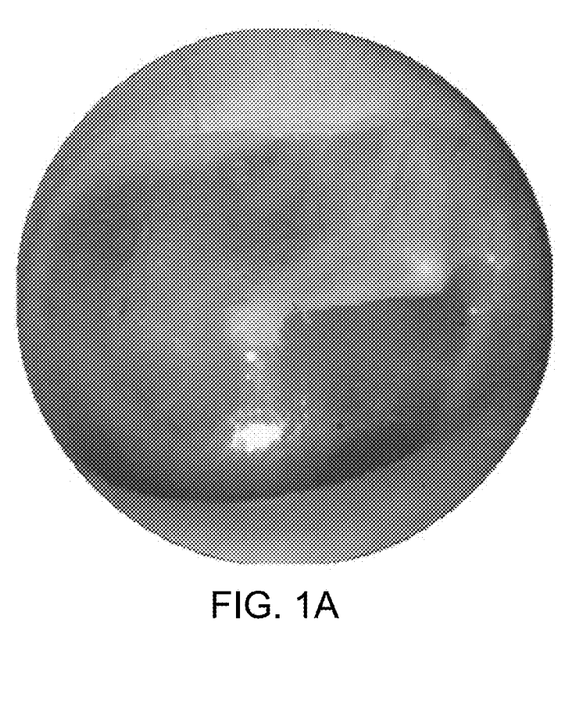
FIGS. 1A-1B illustrate the effect of fogging on images, according to an embodiment.
Figure 1B:
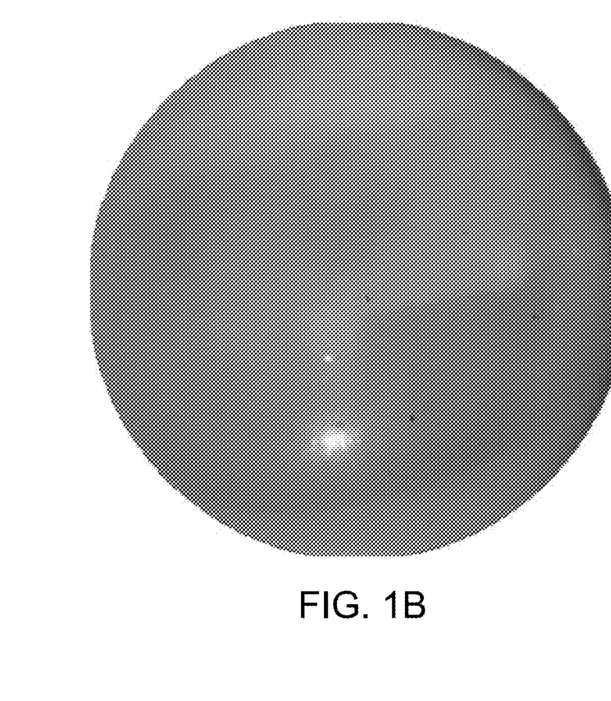

FIGS. 1A-1B illustrate the effect of fogging on images, according to an embodiment. FIG. 1A is an image of a healthy tympanic membrane collected with a lightfield otoscope. FIG. 1B is an image of the same patient tympanic membrane after the front window of the lightfield otoscope has fogged. Between the clear and fogged images, the high frequency spatial features are no longer in focus and the color quality of the image is deteriorating. Spatial features identifiable in FIG. 1A are not identifiable in FIG. 1B. This is detrimental because conditions such as acute otitis media (AOM) and otitis media with effusion (OME) can be diagnosed based on shape, color and/or features of the tympanic membrane.

Figure 2:
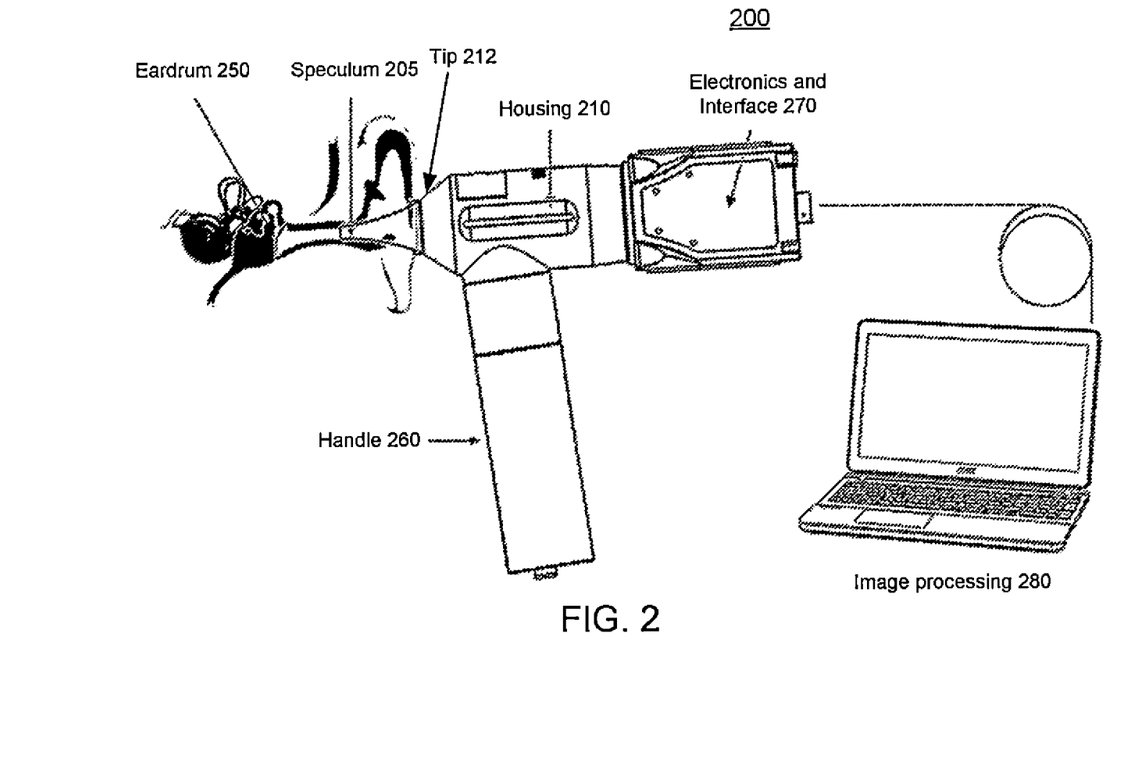
FIG. 2 illustrates a lightfield digital otoscope system, according to an embodiment.

FIG. 2 illustrates use of a lightfield otoscope 200 to image the eardrum 250 of a patient. In this example, the otoscope 200 is handheld and includes a main housing 210 and a handle 260. A disposable speculum 205 is attachable to the tip 212 of the housing 210. In this example, the output of the otoscope 200 is transmitted via electronics and interface 270 to a computer system 280, which processes the captured lightfield images and displays the desired results.

Figure 3A:
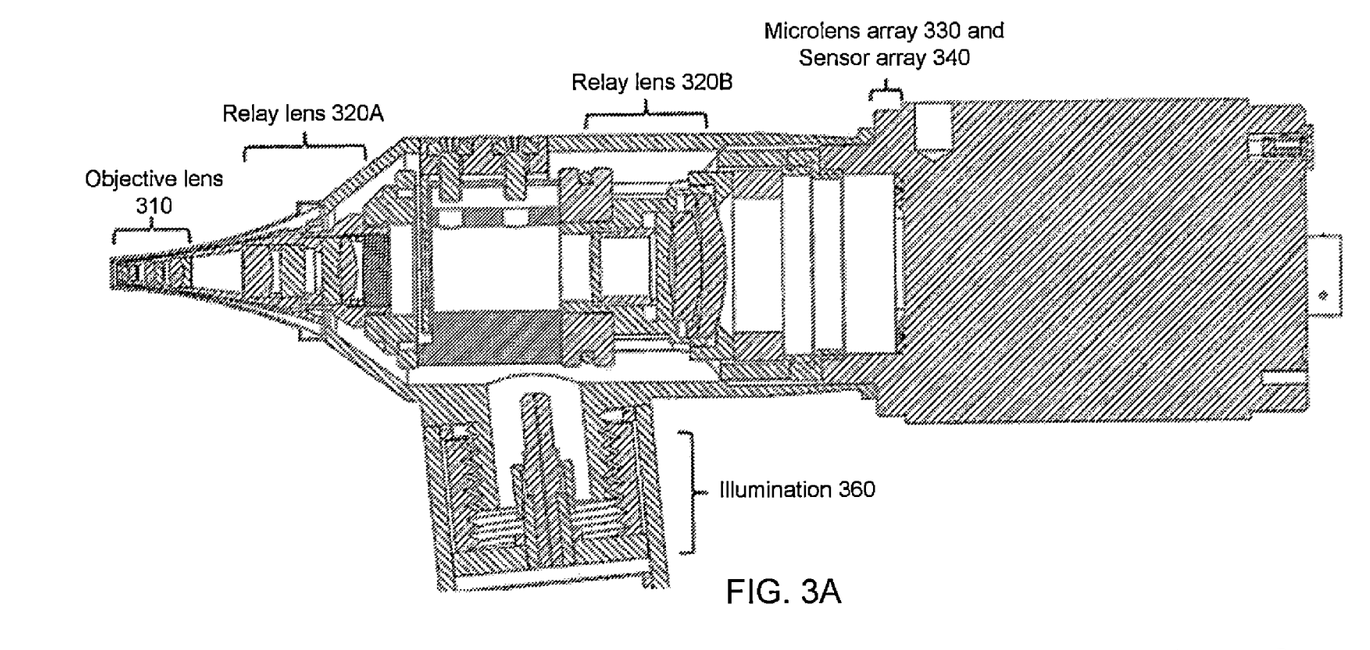
FIG. 3A is a cross-section of a lightfield otoscope, according to an embodiment.
Figure 3B:
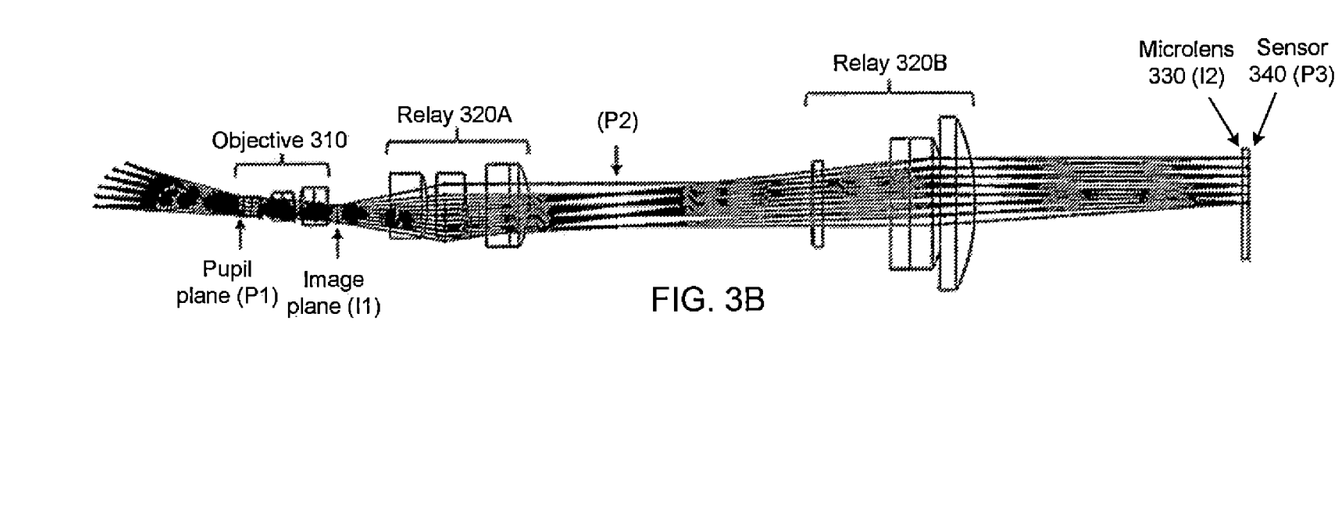
FIG. 3B is a diagram of the optical train from FIG. 3A, according to an embodiment.

The main housing 210 contains the optical train, which is shown in more detail in FIGS. 3A and 3B. The optical train includes an otoscope objective lens 310 and a relay lens 320A-B. Here, the term "lens" is meant to include groups of optical elements. For example, the objective lens 310 includes multiple optical elements, and the relay lens 320 includes two groups of optical elements. The otoscope also includes a microlens array 330 followed by a sensor array 340. The objective lens 310 forms an image of the object of interest (i.e., the tympanic membrane). The relay lens 320 relays this image to the microlens array 330. That is, the microlens array 330 is positioned at a conjugate I2 of the image plane I1 of the objective lens 310. The sensor array 340 is positioned at a conjugate P3 of the pupil plane P1 of the objective lens 310, typically at the focal plane of the microlens array 330. The handle 260 includes an illumination source 360 for the otoscope 200.

The optical train forms two overlapping imaging subsystems. One imaging subsystem images the object onto image plane I1, which is then relayed to the microlens array 330 located at conjugate plane I2. The other imaging subsystem images the pupil plane P1 onto the sensor array 340 located at conjugate plane P3. The system in its entirety forms spatially multiplexed and interleaved optical images at the sensor array 340. For convenience, the image captured by the sensor array 340 will be referred to as a lightfield image. For convenience, the locations of images, apertures and their optical conjugates will be referred to as planes (e.g., image plane, pupil plane), but it should be understood that the surface does not have to be perfectly planar.

The lightfield image has the following structure. The object is imaged onto I2. In conventional imaging, a sensor array at I2 would capture this image. In the lightfield otoscope, a microlens array is located at I2. Each microlens is illuminated by light from a certain region of the object. For example, the center microlens is illuminated by light from the center region of the object. The lightfield image has a structure of superpixels corresponding to the microlenses. Each superpixel captures light from a certain region of the object. The superpixels contain many individual subpixels, which typically correspond to individual sensors in the sensor array. Each subpixel within a superpixel captures light from the same region of the object, but at different propagation angles.

In other words, the object generates a four-dimensional light field $L(x,y,u,v)$, where L is the amplitude, intensity or other measure of a ray originating from spatial location $(x,y)$ propagating in direction $(u,v)$. Each subpixel in the lightfield image captures light from a certain volume of the four-dimensional light field. The subpixels are sampling the four-dimensional light field. The shape or boundary of such volume is determined by the characteristics of the lightfield imaging system.

In certain lightfield imaging system designs, the sample volumes are hyperrectangles. That is, every subpixel within a superpixel captures light from the same rectangular $(x,y)$ region associated with the superpixel, and each subpixel within the superpixel captures light from a different rectangular $(u,v)$ region. However, this is not always the case. For convenience, the superpixels will be described as capturing light from a certain region of the object (even though subpixels within that superpixel may capture light from slightly different regions), and the subpixels will be described as capturing light from a certain range of propagation directions (even though the range may be different for different subpixels, or even for different $(x, y)$ points captured by the same subpixel). Regardless of the details, the sensor array 340 captures a lightfield image, which maps $(x,y)$ spatial locations and $(u,v)$ propagation directions to subpixels. This is in contrast to a conventional image, which maps $(x,y)$ spatial locations to pixels but loses information about the $(u,v)$ propagation directions.

Optionally, a filter module can be positioned at the pupil plane (or one of its conjugates P2 in this example). The filter module can contain a number of spatially multiplexed filter cells, which allows filtering of the lightfield image.

Because the lightfield image contains information about the four-dimensional light field produced by the object, the processing module 280 can be used to perform different types of analysis, such as depth estimation, three-dimensional reconstruction, synthetic refocusing, extending the depth of focus, spectral analysis and other types of multi-view analysis.

The characteristics of a lightfield imaging system can be used advantageously in otoscopes to image the interior of the ear. By using a lightfield imaging system, three-dimensional (3D) shapes, translucency and/or color information can be captured and extracted.

For example, the lightfield otoscope may be operable in a depth imaging mode. In the depth imaging mode, the lightfield image captured by the sensor array is processed to provide a three-dimensional depth image of an inside of an ear. Alternately or additionally, a lightfield otoscope is operable in a spectral imaging mode. In the spectral imaging mode, lightfield data captured by the sensor array is processed to provide two or more different spectral images of an inside of an ear. Disparity or depth maps can also be determined. The lightfield otoscope may be switchable between the depth imaging mode and the spectral imaging mode or operate in both.

The lightfield data can be processed to produce enhanced imagery of the ear interior. Data based on the enhanced imagery can then be used to assist a person in making a medical diagnosis. This diagnostic data could be the enhanced imagery itself or it could involve further processing of the enhanced imagery.

Enhanced imagery of the tympanic membrane is a good example. A lightfield otoscope can simultaneously capture depth and spectral information about the tympanic membrane. A depth map of the tympanic membrane can produce information regarding its shape—whether it is bulging or retracting, and the estimated curvature. Spectral information can include an amber or yellow image, which is especially useful to diagnose conditions of the tympanic membrane.

For example, Table 1 lists some features distinguishing the conditions of acute otitis media (AOM), otitis media with effusion (OME), and otitis media with no effusion. As can be seen from Table 1, the three conditions of the ear are different and they can be distinguished from one another based on one or more of the following features: color, position (e.g., 3D shape), and translucency. In order to make correct diagnosis of the ear condition, otoscopic images capturing accurate information about color, 3D shape and translucency of an inside of an ear (e.g., a tympanic membrane in an ear canal) are desirable. These can all be captured simultaneously by a lightfield otoscope.

TABLE 1

Otoscopic findings associated with clinical diagnostic categories on TM images

| | AOM | OME | NOE |
|---|---|---|---|
| Color | White, pale yellow, markedly red | White, amber, gray, blue | Gray, pink |
| Position | Distinctly full, bulging | Neutral, retracted | Neutral, retracted |
| Translucency | Opacified | Opacified, semi-opacified | Translucent |

Lightfield data also includes multiple views of the same image. This allows the user to refocus to different depths in the image and to view the same image from different viewpoints. For example, the effect of occluding objects may be reduced by taking advantage of multiviews. This could be accomplished by refocusing. Alternately, it could be accomplished by segmenting the lightfield (multiple views) into depth layers.

Figure 4:
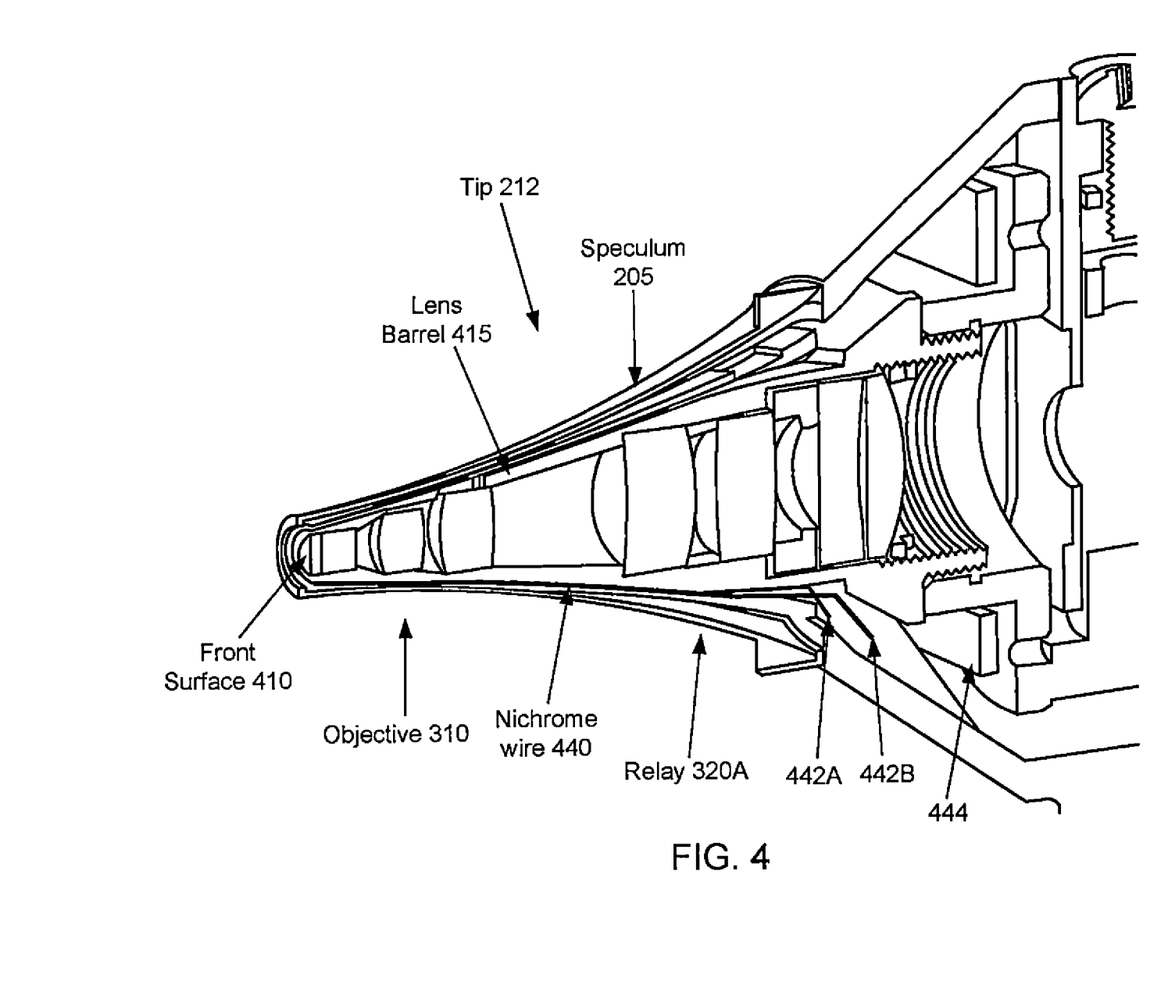
FIG. 4 is a diagram of a lightfield otoscope with an anti-fogging heating element, according to an embodiment.

However, as mentioned previously, the ear canal can be hot and humid. Fogging and condensation on the front surface of the lightfield otoscope can degrade the quality of the captured images. FIG. 4 is a diagram of a lightfield otoscope with an anti-fogging heating element, according to an embodiment. FIG. 4 shows the tip 212 of the otoscope housing, with a speculum 205 mounted on the tip. The objective 310 and relay 320A elements of the optical train are also shown. The objective lens 310 is held in a lens barrel 415, which is made of a thermally conductive material. The housing contains a nichrome wire 440, which is positioned to heat the front surface 410 of the optical train, thereby reducing fogging and condensation. A controller, for example implemented on printed circuit board 444, controls current to the nichrome wire 440. As the wire generates heat, the heat is conducted through the lens barrel 415 to the front surface 410. An insulating layer, such as the disposable speculum 205, shields the patient's ear drum from heating by the wire.

In more detail, the two ends 442A,B of the wire 440 are located in the base of the tip (i.e., the part that is away from the ear). The wire 440 runs along the lens barrel from the base to the front surface and back, so that a mid-section of the wire is located near the front surface. The two ends 442 are connected to the controller, for example electronic circuitry that regulates the current running through the wire 440. Because this is an otoscope application, the controller controls the heating to avoid any injury to the patient. In addition, the controller has an operating range that includes at least 36-40 degrees Celsius, since those are typical conditions to be encountered.

Heating can be manually controlled. For example, the otoscope might have a button that is pressed by the operator to activate heating. Alternatively, the active heating element may run continuously during operation of the otoscope to maintain the front surface 410 at a high temperature to avoid fogging, even without manual instructions from the operator. In some cases, the controller may control the heating element based on environmental conditions in the vicinity of the front surface 410, for example the temperature or humidity in this vicinity.

Figure 5:
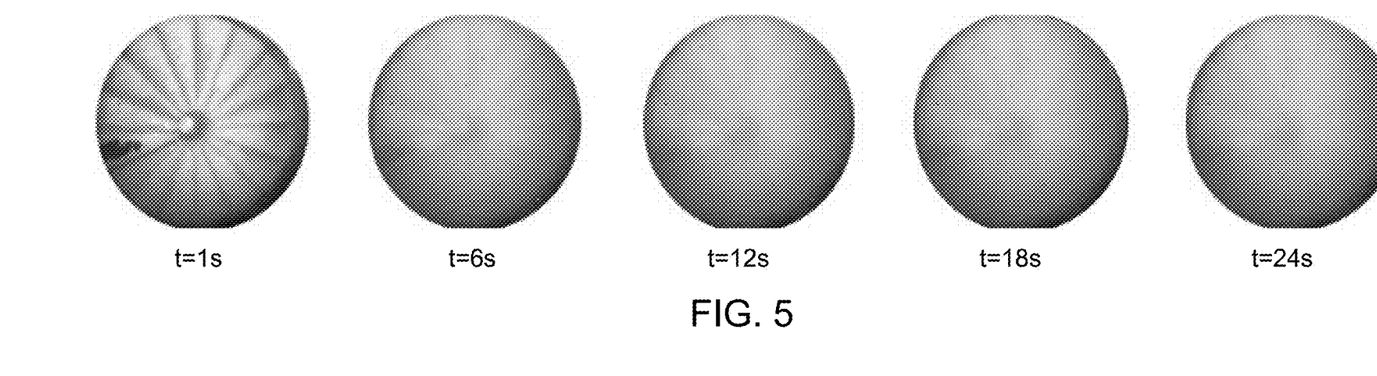
FIG. 5 is a sequence of images of an ear canal phantom taken over time in the presence of fogging, according to an embodiment.

In yet another approach, heating is controlled based on the quality of the captured images. FIG. 5 is a sequence of images of an ear canal phantom taken over time in the presence of fogging when the active heater is off. Condensation on the front surface 410 fogs the image. The photos are taken approximately every six seconds. The ear canal phantom is 15 mm long and 10 mm in diameter. At the end of the ear canal is a set of pie-shaped wedges arranged in the shape of a spiral staircase. Each step is 300 μm tall. This is a phantom for the ear drum. The design is based on FEM analysis and physiological studies of ear anatomy. The experimental setup is also capable of holding a temperature and humidity probe to measure the environmental conditions in the phantom ear canal. This ear canal phantom was set to 40.2° C. and 104% humidity. A lightfield otoscope was used to produce the images in FIG. 5 over a period of 24 seconds. The images clearly show fog forming over the image.

Figure 6A:
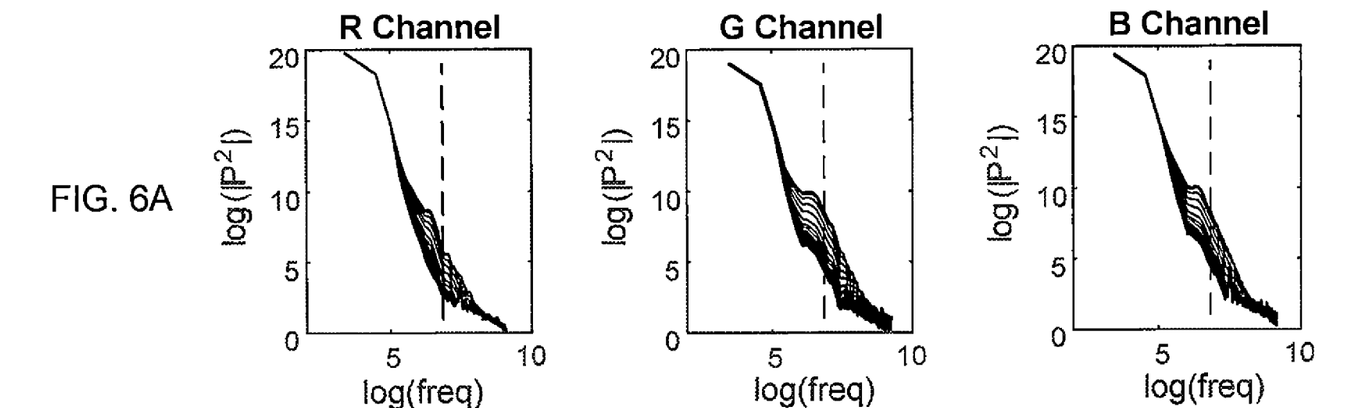
FIG. 6A shows the power spectra for red, green and blue channels taken over time in the presence of fogging, according to an embodiment.

FIGS. 6A and 6B show the corresponding power spectra. FIG. 6A (top row of three graphs) shows the power spectra. The left graph is for the red component, the middle graph is for the green component and the right graph is for the blue component. Each graph shows a series of curves. Each curve is for a different time. The top curve is for the earliest time (least fogging) and the bottom curve is for the latest time (most fogging). The x-axis is log(spatial frequency) where the spatial frequency is measured in 1/mm, and the y-axis is log($P^2$).

Figure 6B:
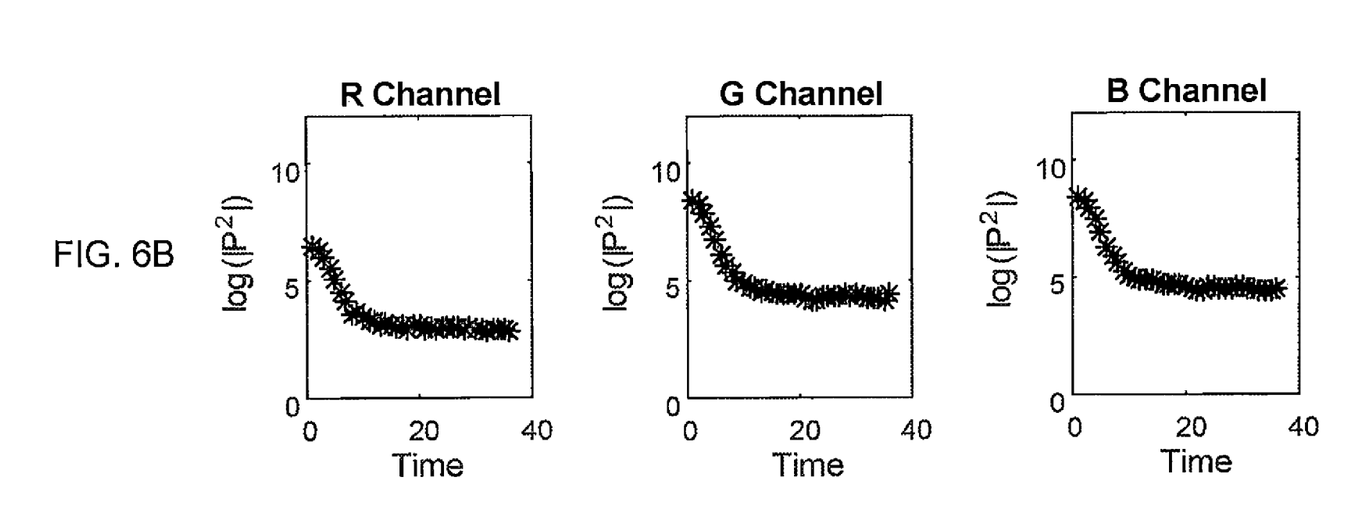
FIG. 6B shows the power as a function of time for one specific frequency, according to an embodiment.

FIG. 6B (bottom row of three graphs) plots the power at one specific spatial frequency over time (in seconds). Again, the left graph is for the red component, the middle graph is for the green component and the right graph is for the blue component. The selected frequency is shown by the dashed line in FIG. 6A. It is a frequency that exhibits a large degradation due to the fogging. The strength of the spatial frequency decreases over time in all three color channels.

In FIGS. 6A-B, the power spectra for each color channel is determined as follows. The captured lightfield image is cropped to remove null space in the image. The image has a circular region of interest. This feature would appear as a high frequency signal in Fourier space. A smoothing window applied to the image reduces the impact of the high frequency feature. A commonly used smoothing window is the Hann window. This is applied to the image g and a discrete Fourier transform G is taken. The power spectra is recovered from the absolute value of the square of G. Radial samples of G are collected to record the average power spectra. In FIG. 6 above, 400 radial samples of P were collected and plotted on a log-log scale.

Measuring the power spectra of the R, G, and B channels over time monitors the intensity of spatial frequency contributions in the image. This can be used to control the heating element. This is just one example based on the power spectra of the images. In other approaches, control can be based on a wavelet analysis of the images, or on a gradient analysis of the images, or on a contrast of the images, or on other measures of the spatial frequency content of the images. In these cases, the controller may be a microcontroller or embedded processor, rather than a simple feedback loop.

Figure 7:
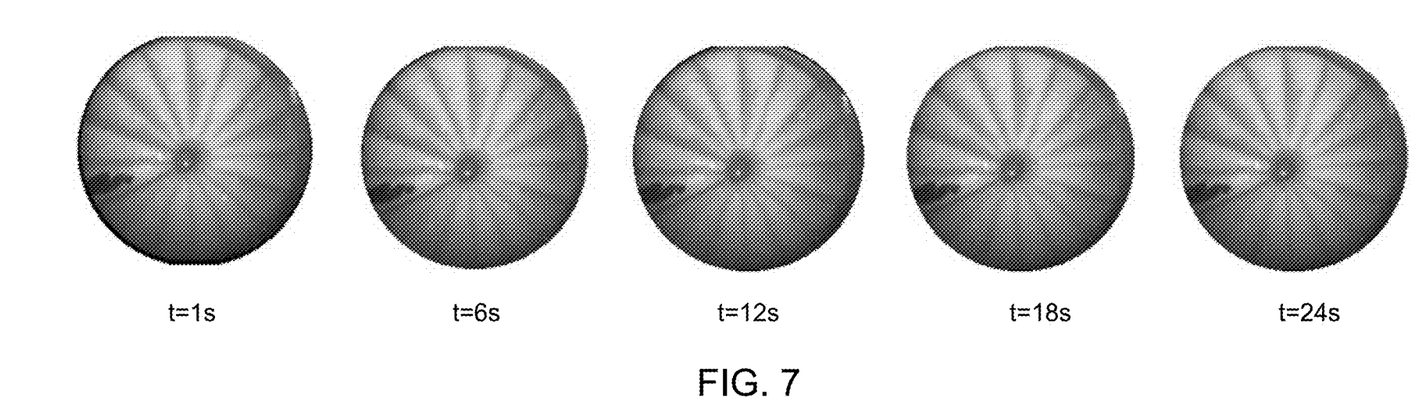
FIG. 7 is a sequence of images of an ear canal phantom taken over time while using an active heater element, according to an embodiment.
Figure 8A:
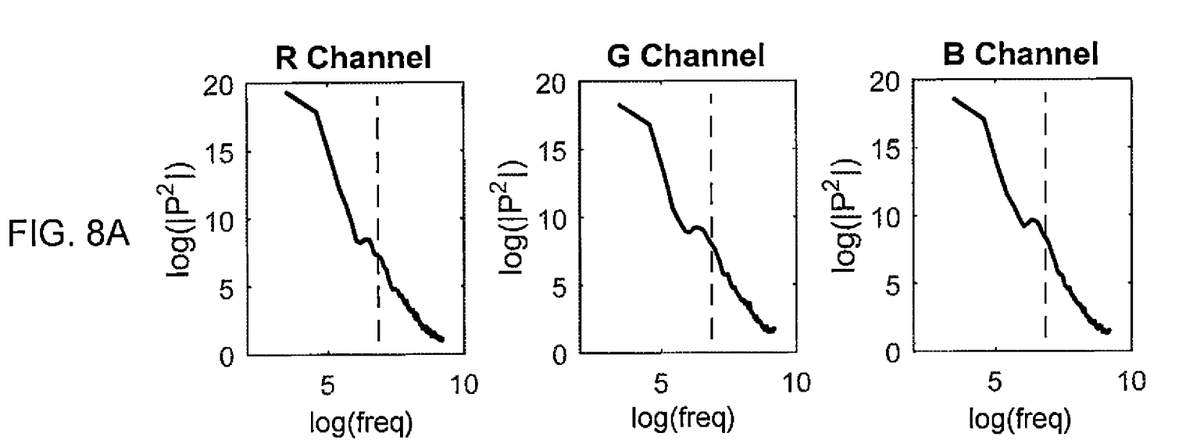
FIG. 8A shows the power spectra for red, green and blue channels taken over time while using an active heater element, according to an embodiment.
Figure 8B:
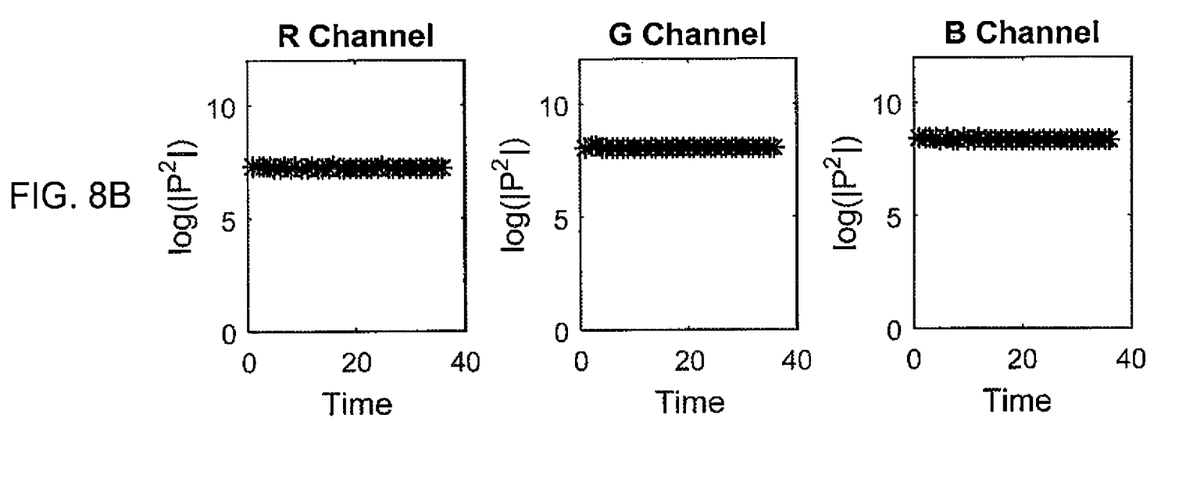
FIG. 8B shows the power as a function of time for one specific frequency, according to an embodiment.

FIGS. 7-8 show the same plots as FIGS. 5-6, but with the active heater element turned on. The ear canal phantom was set to 41.7° C. and 97% humidity. A lightfield otoscope was used to produce the images in FIG. 7 over a period of 24 seconds. The heating element is active, preventing fog to collect on the front optical surface. The images clearly show clear images over time.

FIG. 8A shows power spectra results for red, green and blue components. The curves for different times are not distinguishable. FIG. 8B plots the power at one specific spatial frequency over time, for red, green and blue components. The selected frequency is shown by the dashed line in FIG. 8A. It is the same frequency as selected in FIG. 6. The strength of the spatial frequency remains almost constant over time in all three channels.

Figure 9A:
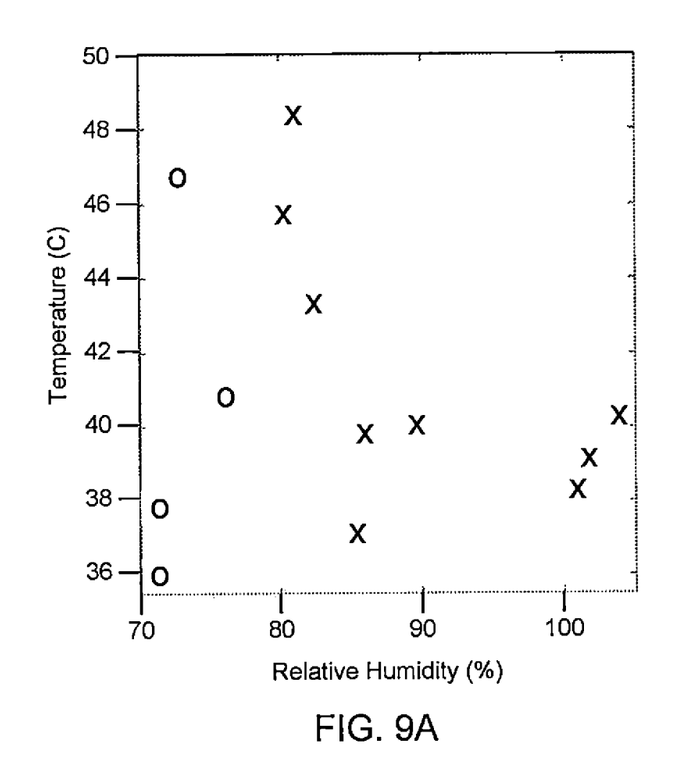
FIG. 9A plots different trials with the heater element off, according to an embodiment.
Figure 9B:
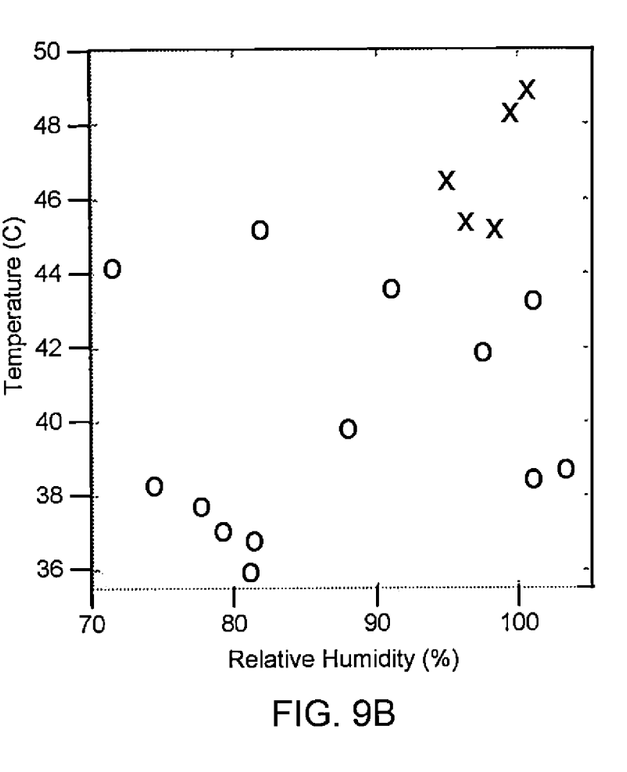
FIG. 9B plots different trials with the heater element on, according to an embodiment.

Experiments using the ear canal phantom were repeated over a range of 36-45° C. and 70-105% humidity, with the heating element on and off. For each trial, we observe whether the image remains foggy or clear. A clear image is a success and is marked by a circle in FIGS. 9A-9B. A foggy image is a failure and is marked by an x in FIGS. 9A-9B. The results of these trials are shown in FIGS. 9A and 9B. FIG. 9A are the trials with the heating element off. Fogging is apparent starting around 80% humidity. FIG. 9B are the trials with the heating element on. Fogging is significantly improved.

Although the detailed description contains many specifics, these should not be construed as limiting the scope of the invention but merely as illustrating different examples and aspects of the invention. It should be appreciated that the scope of the invention includes other embodiments not discussed in detail above. For example, the approach described above is not limited to nichrome wires. Other active heating elements include metal heating elements, ceramic heating elements, resistive heating elements, thin film heating elements, wire heating elements. Examples of materials include kanthal and cupronickel in addition to nichrome.

In addition, this approach can also be used with other imaging systems, including other lightfield systems and also conventional imaging systems. For example, imaging systems used in body cavities include endoscopes and otoscopes. Other imaging systems may be designed for use in steam environments, or high temperature or high humidity environments. The ability to automatically defog a camera removes the need for a human to access a camera in a location that is difficult to access. Temperature and humidity sensors can be used to automatically regulate the temperature of the optics based on the surrounding environmental conditions. One example is an outdoor security camera, where weather is constantly changing and condensation can occur naturally.

Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A lightfield otoscope comprising:
a housing with a tip configured to receive a disposable speculum;
a microlens array and a sensor array, the microlens array including microlenses each configured to provide light from a region of an object at different propagation angles to different sensors of the sensor array;
an optical train contained within the housing, the optical train having a front surface and comprising an objective lens and relay lens, the objective lens positioned at least partially within the tip, the relay lens positioned to relay an image plane of the objective lens to the microlens array and to relay a pupil plane of the objective lens to the sensor array; and
an active heating element controlled by a controller, the active heating element contained within the housing and positioned to heat the front surface, thereby reducing fogging and/or condensation on the front surface, wherein the controller controls the active heating element using power spectra of images captured by the lightfield otoscope.

2. The lightfield otoscope of claim 1, wherein
the controller controls the active heating element using a humidity in a vicinity of the front surface captured by a sensor.

3. The lightfield otoscope of claim 1 further comprising a lens barrel that holds the objective lens, the active heating element heating the lens barrel and the lens barrel conducting heat to the front surface.

4. The lightfield otoscope of claim 1 wherein the active heating element is a resistive wire having two ends and a mid-section, the two ends located in a base of the tip and connected to the controller, the mid-section located near the front surface, and the wire running from the base to the front surface and back.

5. The lightfield otoscope of claim 1 wherein the controller controls the active heating element to avoid injury to a human ear canal.

6. The lightfield otoscope of claim 1 wherein the controller has an operating range that includes 36-40 degrees Celsius.

7. The lightfield otoscope of claim 1 further comprising:
an insulating layer positioned to shield an external environment from heating by the active heating element.

8. The lightfield otoscope of claim 1 wherein the active heating element includes at least one of a metal heating element and a ceramic heating element.

9. The lightfield otoscope of claim 1 wherein the active heating element includes at least one of a resistive heating element, a resistive wire and a thin film heating element.

10. The lightfield otoscope of claim 1 wherein the active heating element comprises at least one of nichrome, kanthal and cupronickel.

11. The lightfield otoscope of claim 1 wherein the controller comprises an electronic circuit.

12. The lightfield otoscope of claim 1 wherein the controller comprises a microcontroller.

13. A digital imaging system comprising:
an optical train that forms an image of an object, the optical train having a front surface;
a sensor array that captures the image of the object; and
an active heating element controlled by a controller, the active heating element mounted with the optical train and positioned to heat the front surface, thereby reducing fogging and/or condensation on the front surface, wherein the controller controls the active heating element using power spectra of images captured by the digital imaging system.

14. The digital imaging system of claim 13 wherein the digital imaging system is a lightfield digital imaging system.

15. The digital imaging system of claim 13 wherein the digital imaging system is a digital otoscope.

16. The digital imaging system of claim 13 wherein the digital imaging system is adapted to be used in a steam environment, a high temperature environment or a high humidity environment.

* * * * *